United States Patent [19]

Hoch

[11] Patent Number: 5,313,952
[45] Date of Patent: May 24, 1994

[54] ELECTRODE ATTACHMENT APPARATUS

[76] Inventor: Richard W. Hoch, 1017 Park Ave., Mahtomedi, Minn. 55115

[21] Appl. No.: 949,434

[22] Filed: Sep. 23, 1992

[51] Int. Cl.⁵ .............................................. A61B 5/0408
[52] U.S. Cl. ...................................................... 128/644
[58] Field of Search ............... 128/644, 639, 802, 791, 128/792, 384, 385, 388; 607/139, 140, 149

[56] References Cited

U.S. PATENT DOCUMENTS

| | | | |
|---|---|---|---|
| 2,842,136 | 7/1958 | Browner | 128/791 |
| 4,026,278 | 5/1977 | Ricketts et al. | 128/388 X |
| 4,391,279 | 7/1983 | Stein | 128/644 |

FOREIGN PATENT DOCUMENTS

0396048  11/1990  European Pat. Off. ............ 128/644

*Primary Examiner*—Lee S. Cohen
*Attorney, Agent, or Firm*—Lawrence M. Nawrocki

[57] ABSTRACT

An electrode belt assembly for positioning an electrically conductive electrode against the body member of a patient, particularly an infant, includes a flexible web belt having a plurality of apertures therein and an electrode pad assembly that can be selectively positioned in a desired aperture. The electrode pad assembly includes a disk pad having a receptacle that is received within a selected aperture in a form fit and a lead probe assembly receivable within the receptacle. The receptacle presents a probe receiving channel oriented generally parallel to the surface of the belt. The engagement of the disk pad and lead probe assembly with the opposed surfaces of the belt, together with the form fit of the receptacle within a selected aperture, provide for a secure positioning of the electrode pad on the belt.

4 Claims, 2 Drawing Sheets

ELECTRODE ATTACHMENT APPARATUS

FIELD OF THE INVENTION

The present invention deals broadly with attachment of electrodes to human body members. More specifically, however, the invention is related to electrode monitoring of the vital signs of an infant, and more particularly, an infant born prematurely. The preferred embodiment of the invention is directed to an adjustable foam cloth belt including a plurality of apertures therethrough for selective, removable placement of an electrode pad along the length of the belt.

BACKGROUND OF THE INVENTION

Critical care monitoring of infants and other patients requiring constant care frequently involves electrode-based monitoring of cardiac and respiratory electrophysiological signals. Numerous electrode configurations have been described in the prior art; however, a typical configuration frequently encountered in acute care of premature infants, for example, comprises an electrode pad held in place by a flexible belt. The pad can be of any desired electrically conductive flexible material such as polyvinylchloride impregnated with carbon powder.

Typically the electrode engagement with the infant's skin is effected with the electrode pad in a dry condition. However, it is possible to place a small amount of water or an electro-conductive gel between the skin and the electrode pad in order to facilitate electrical conduction and signal strength and accuracy. Frequently such electrodes are also provided with a pressure sensitive adhesive which functions to hold the electrode pad and, if necessary, the electrode gel, in contact with the infant's skin. Particularly in the case of infants, such adhesives can prove irritating and necessitate interruption of continuous monitoring to allow recovery from the irritation.

Other problems are encountered when using conventional electrode attachment assemblies in the care of infants. It is often difficult to precisely and properly place the electrode pad of conventional electrode attachment assemblies on the small body members of infants. More particularly, the relationship between the placement of the electrode pad along the length of the belt and the coupling mechanism attaching one end of the belt to the other for securing the belt to a body member may not allow for appropriate placement of the electrode pad. A related problem is the requirement to securely hold the pad in a designated place along the infant's body member. The secureness of the attachment may be compromised in an effort to properly place the pad on the body member. Finally, a large percentage of the infant's body member part may be covered by even a narrow strip web belt. Proper ventilation of the infant's skin is thereby compromised.

An electrode attachment apparatus that provided for precise positioning of an electrode pad along an infant's body member, which could be securely held in place in the desired position, and which provided for proper ventilation of an infant's small body parts would provide decided advantages.

SUMMARY OF THE INVENTION

The problems outlined above are in large measure solved by the electrode belt assembly for positioning an electrically conductive electrode pad against the body member of a patient in accordance with the present invention. The belt assembly includes a web belt having a length sufficient to detachably encircle the body member and having a plurality of apertures extending through the belt along the belt length.

The electrode pad of the assembly includes a protruding receptacle that can be received through a selected one of the apertures along the length of the belt. The receptacle presents a lead receiving channel oriented generally parallel to the surface of the belt. A probe element of a electrically conducting lead is received within the channel, and the electrode pad is held in place along the belt by the engagement of the pad and the lead with the opposed surfaces of the belt, and the form fit of the receptacle within the aperture. The plurality of apertures provides for selective positioning of the electrode pad anywhere along the length of the belt, and also provides for proper ventilation of the body member around which the belt is wrapped.

DETAILED DESCRIPTION OF THE DRAWINGS

Figure 1:
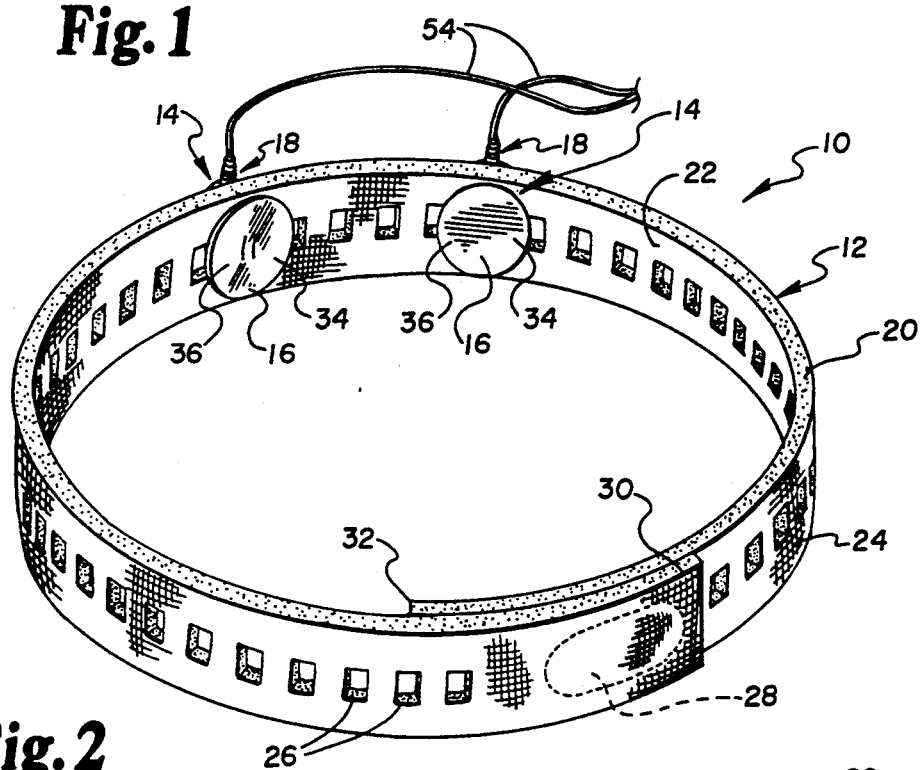
FIG. 1 is perspective view of an electrode belt assembly in accordance with the present invention showing a pair of electrode pads mounted at selected positions along the web belt of the assembly.

Referring now to the drawings, wherein like reference numerals denote like elements throughout the several views, FIGS. 1-5 illustrate the components comprising a first embodiment of the apparatus in accordance with the present invention. FIGS. 6-9 illustrate the components comprising an alternative embodiment of the apparatus in accordance with the present invention.

Referring to FIGS. 1-5, the electrode belt assembly 10 in accordance with the first embodiment of the invention broadly includes web belt 12 and electrode pad assembly 14. The electrode pad assembly 14 includes electrode disk pad 16 and lead probe assembly 18 detachably received by the disk pad 16.

The web belt 12 comprises an elongated foam material strip 20 sandwiched between inner and outer cloth backing strips 22, 24. Apertures 26 are generally evenly spaced along the length of the belt 12. The apertures 26 are preferably noncircular, and in the embodiments depicted in the drawing comprise generally square channels extending between the inner and outer surfaces of the belt 12. Referring to FIG. 1, an attachment mechanism 28 for attaching the lead end 30 of the belt 12 to the trailing end 32 of the belt 12 is depicted in phantom lines. The attachment mechanism 28 can comprise a Velcro ® brand hook and mesh system, metal snaps, or any other suitable attachment mechanism.

Figure 2:
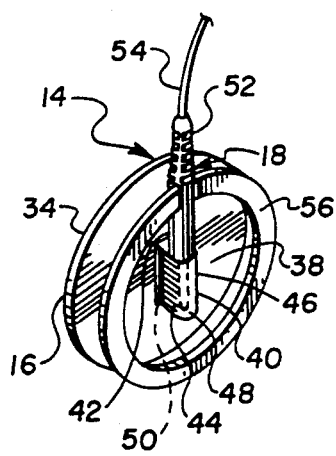
FIG. 2 is a perspective view of an electrode pad and lead probe assembled together separate from the web belt of the electrode belt assembly.
Figure 3:
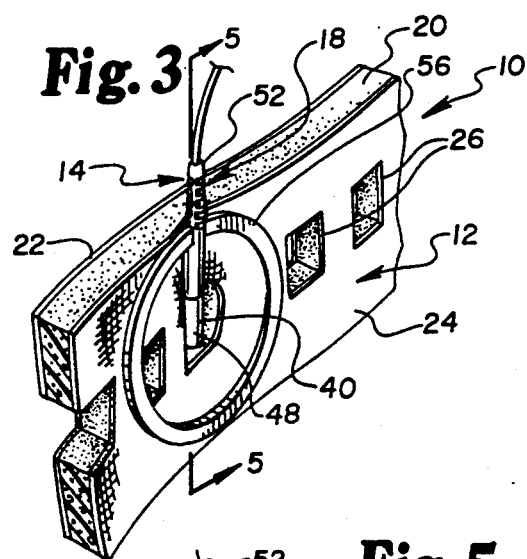
FIG. 3 is a fragmentary, perspective view of an electrode pad and lead assembly coupled together and mounted on a web belt.

The disk pad 16 comprises a generally circular, flat disk 34 having a body member engaging surface 36 and an opposed surface 38. A receptacle element 40 protrudes outwardly from the opposed surface 38 of the electrode pad disk 34. The receptacle element 40 defines a probe receiving channel 42 having a longitudinal axis oriented generally parallel to the surface 38 of the disk 34. The cross section of the receptacle element 40 matches the shape of the apertures 26 of the belt 12 such that the receptacle element 40 can be received within a selected aperture 26 in a form fit. Referring in particular to FIG. 2, it will be seen that the receptacle element 40 includes opposed, generally planar side walls 44, 46 and arcuate end wall 48 which together define the probe receiving channel 42.

Figure 4:
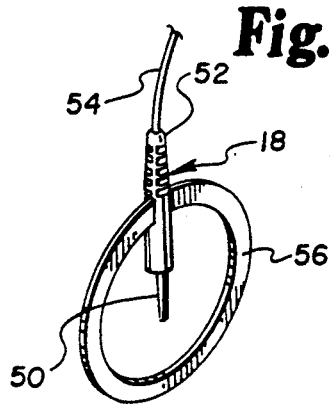
FIG. 4 is a perspective view of the lead probe.
Figure 5:
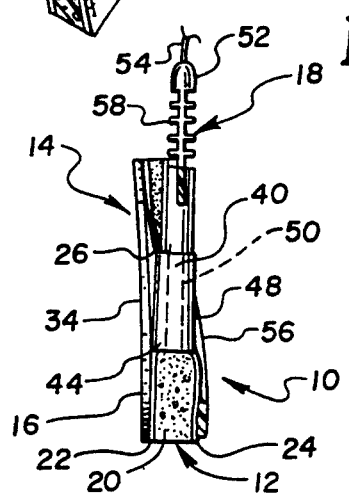
FIG. 5 is a sectional view taken along the line 5—5 of FIG. 3.
Figure 7:
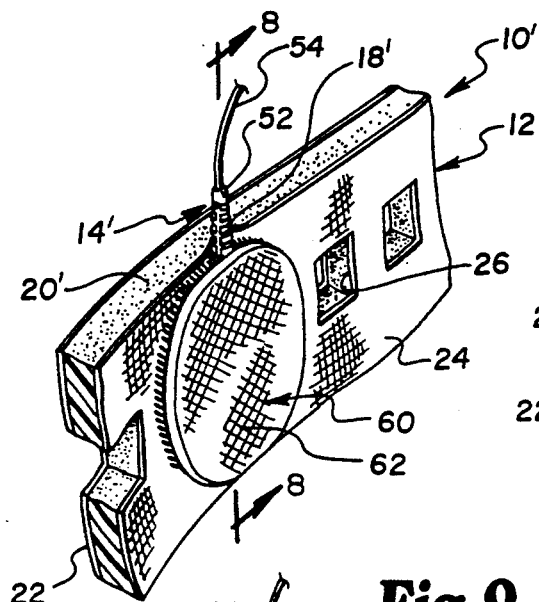
FIG. 7 is similar to FIG. 6 but depicted with a covering patch over the lead probe.
Figure 6:
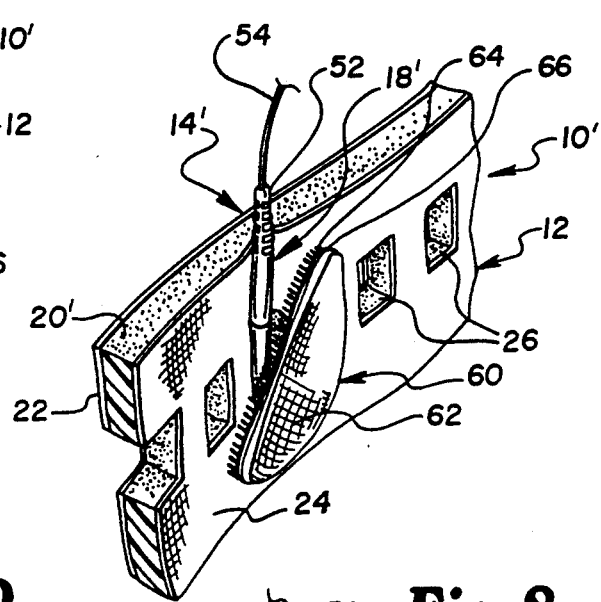
FIG. 6 is a perspective view of a second embodiment of an electrode belt assembly having an alternative lead probe design.
Figure 9:
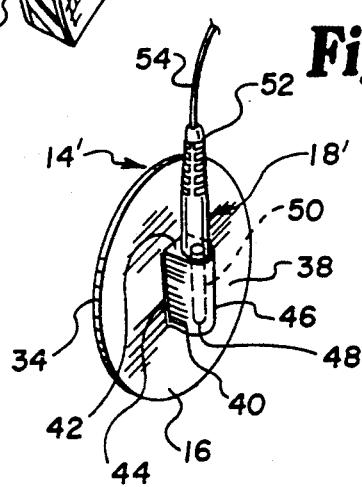
FIG. 9 is perspective view of an electrode pad and lead probe in accordance with the alternative embodiment, shown coupled together without the web belt.
Figure 8:
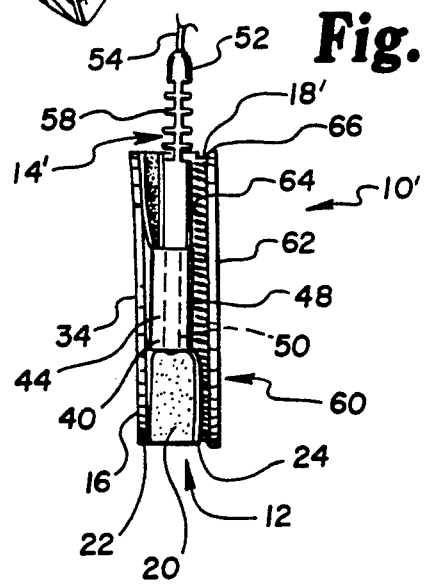
FIG. 8 is a sectional view taken along the line 8—8 of FIG. 7.

Referring to FIG. 4, lead probe assembly 18 includes probe 50 receivable within channel 42 of disk pad 16, probe support element 52 generally aligned with the lead probe 50, coupling wire 54 extending from the probe 50, and generally circular support ring 56. Support ring 56 is fixedly coupled to the probe support 52 and comprises a generally flat, annular ring oriented generally parallel to and generally encircling the lead probe 50. Referring in particular to FIG. 5, it will be seen that the support ring is generally flexibly, bendably supported on the probe support 52. Also referring to FIG. 5, it will be seen that crimping ribs 58 are formed on the probe support 52.

An alternative embodiment of the belt assembly 10' is depicted in FIGS. 6-9. It will be seen that the alternative embodiment 10' includes, for the most part, identical elements to those shown and described in conjunction with the first embodiment 10. Like elements are accordingly annotated with the same numerals as the numerals used in conjunction with the first embodiment. The lead probe assembly 18' of the second embodiment 10', however, does not include a support ring 56 as described in conjunction with the first embodiment. The second embodiment 10', moreover, is provided with a cover pad 60 that includes a cloth backing material 62 and a Velcro ® patch 64 presenting hooks 66 for attachment to outer backing strip 24 of belt 12 in a hook and mesh type arrangement.

In operation, the electrode pad assembly 14 comprising the disk pad 16 and lead probe assembly 18 are positioned along the belt 12 at a desired position by first inserting the receptacle element 40 of the disk pad 16 through a selected aperture 26 of the belt 12. The lead probe 50 of the lead probe assembly 18 is then inserted into the channel 42 defined by the receptacle element 40. The opposed surface 38 of the electrode pad circular 34 engages the inner, or body engaging surface defined by cloth strip 22 of the belt 12, and the lead probe support 42 engages the outer surface defined by the cloth strip 24 of the belt 12. The engagement of the inner and outer surfaces of the belt, together with the form fit of the receptacle element 40 as received through the selected aperture 26 firmly hold the electrode pad assembly 14 in place along the belt 12.

Additional support is provided to the mounting of the electrode pad assembly 14 on the belt 12, in the instance of the first embodiment depicted in FIGS. 1-5, by the engagement of support ring 56 with the outer surface of belt 12. Additional support is provided, in the case of second embodiment depicted in FIGS. 6-9, by the placement of the cover pad 60 over the lead probe assembly 18'.

The use of the present invention has several distinct advantages over the prior art. The electrode pad assembly 14 can be precisely positioned at any point along the length of the belt 12 by selecting the optimum aperture 26. Such flexibility and positioning is particularly advantageous when small body members, such as the arms or legs of small infants, require precise placement of an electrode. The form fit of the receptacle element 40 within the apertures 26, together with engagement of the belt inner and outer surfaces by the disk pad 16 and lead probe assembly 18 provide for secure positioning of the electrode pad on the belt 12 in a simple and effective manner. The presence of the support ring 56 in the first embodiment, and the use of a cover pad 16 in the second embodiment add to the secure positioning of the electrode pad assembly 14 along the belt 12. The perforations in the belt presented by apertures 26 provide for ventilation of the body member to which the electrode pad is attached.

Numerous characteristics and advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. An electrode belt assembly kit for positioning an electrically conductive electrode against a body member of a patient, comprising:

an electrode pad having a body member engaging surface and a receptacle element operably connected to the pad and extending opposite the body engaging surface, the receptacle element defining therewithin a probe element receiving channel;

a web belt having a length sufficient to detachable encircle the body member, the belt including an inner surface, an oppositely facing outer surface and a plurality of apertures extending through the belt from the inner surface to the outer surface, each aperture being adapted for removably receiving the receptacle element in a form fit;

a lead probe having an elongated probe element extending therefrom and adapted for detachable insertion into the probe element receiving channel; and an outer surface engaging support element defining a plane generally parallel to the probe element and being rigidly connected to the lead probe, wherein the receptacle element of the electrode pad is insertable through a selective one of the apertures with the body member engaging surface disposed overlying the inner surface of the belt, and the outer surface engaging support element overlying and being in engagement with the outer surface of the belt when the probe element is received within the probe element receiving channel to hold the electrode pad receptacle element in the selective aperture.

2. The invention as claimed in claim 1, wherein the body member engaging surface comprises a conductive disk for contacting engagement with the body member.

3. The invention as claimed in claim 1, the receptacle element and the apertures being non-circular in shape, so that the receptacle element is non-rotatable relative to the belt when received within one of the apertures.

4. The invention as claimed in claim 1, the plurality of apertures extending generally along the length of the web belt.

* * * * *